US00PP18026P2

(12) United States Plant Patent
Dümmen

(10) Patent No.: US PP18,026 P2
(45) Date of Patent: Sep. 11, 2007

(54) ***GERANIUM* PLANT NAMED 'DUEIMVIDARED'**

(50) Latin Name: *Pelargonium×hortorum*
Varietal Denomination: Dueimvidared

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 11/349,642

(22) Filed: Feb. 7, 2006

(51) Int. Cl.
*A01H 5/00* (2006.01)

(52) U.S. Cl. ..... Plt./330
(58) Field of Classification Search ..... Plt./330
See application file for complete search history.

(56) References Cited

U.S. PATENT DOCUMENTS

| | | | | | |
|---|---|---|---|---|---|
| PP7,897 | P | * | 6/1992 | Winner | Plt./330 |
| PP13,906 | P2 | * | 6/2003 | Dummen | Plt./330 |
| PP16,105 | P2 | * | 11/2005 | Brown | Plt./356 |
| PP16,508 | P2 | * | 5/2006 | Trees | Plt./330 |

OTHER PUBLICATIONS

UPOV ROM GTITM Computer Database, GTI Jouve Retrieval Software 2006/05 Citation for 'Dueimvidared'.*

* cited by examiner

*Primary Examiner*—Wendy Haas
(74) *Attorney, Agent, or Firm*—C. A. Whealy

(57) ABSTRACT

A new and distinct cultivar of Zonal *Geranium* plant named 'Dueimvidared', characterized by its upright, somewhat outwardly spreading and rounded plant habit; vigorous growth habit; freely branching habit; freely and early flowering habit; and dark red-colored double flowers.

1 Drawing Sheet

Botanical denomination: *Pelargonium×hortorum.*
Cultivar designation: 'Dueimvidared'.

BACKGROUND OF THE INVENTION

The present invention relates to a new and distinct cultivar of Zonal *Geranium* plant, botanically known as *Pelargonium×hortorum,* and hereinafter referred to by the name 'Dueimvidared'.

The new Zonal *Geranium* is a product of a planned breeding program conducted by the Inventor in Rheinberg, Germany. The objective of the breeding program was to develop new freely and early flowering Zonal *Geraniums* with attractive flower and foliage colors.

The new Zonal *Geranium* originated from a cross-pollination made by the Inventor on July 1, 1998, of a proprietary selection of *Pelargonium×hortorum* identified as code number F-19-15, not patented, as the female, or seed, parent with a proprietary selection of *Pelargonium×hortorum* identified as code number F-04-09, not patented, as the male, or pollen, parent. The cultivar Dueimvidared was discovered and selected by the Inventor as a flowering plant within the progeny from this cross-pollination in a controlled environment in Rheinberg, Germany on Jun. 1, 2003.

Asexual reproduction of the new cultivar by terminal vegetative cuttings at Rheinberg, Germany since Jul. 1, 2003, has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Dueimvidared'. These characteristics in combination distinguish 'Dueimvidared' as a new cultivar and distinguish it from other known Zonal *Geranium* cultivars:

1. Upright, outwardly spreading and rounded plant habit.
2. Vigorous growth habit.
3. Freely branching habit.
4. Freely and early flowering habit.
5. Dark red-colored double flowers.

Compared to plants of the female parent selection, plants of the new Zonal *Geranium* are more vigorous. In addition, plants of the new Zonal *Geranium* and the female parent selection differ in flower color as plants of the female parent selection have pink-colored flowers. Compared to plants of the male parent selection, leaves of plants of the new Zonal *Geranium* do not have a visible leaf zonation pattern whereas plants of the male parent selection have a distinct leaf zonation pattern. In addition, plants of the new Zonal *Geranium* and the male parent selection differ in flower color as plants of the male parent selection have orange red-colored flowers.

The new Zonal *Geranium* can be compared to plants of the cultivar Duevidared, disclosed in U.S. Plant Pat. No. 13,906. In side-by-side comparisons conducted in Rheinberg, Germany, plants of the new Zonal *Geranium* differed from plants of the cultivar Duevidared in the following characteristics:

1. Plants of the new Zonal *Geranium* were more vigorous than plants of the cultivar Duevidared.
2. Leaves of plants of the new Zonal *Geranium* did not have a visible leaf zonation pattern whereas leaves of plants of the cultivar Duevidared had a distinct leaf zonation pattern.
3. Plants of the new Zonal *Geranium* had larger flowers than plants of the cultivar Duevidared.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Dueimvidared' grown in a container.

DETAILED BOTANICAL DESCRIPTION

The cultivar Dueimvidared has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were pinched once about three weeks after planting. Plants were about eight weeks from unrooted cuttings when the photograph and the detailed botanical description were taken. In the following description, color references are made to The Royal Horticultural Society Colour Chart, 1995 edition, except where general terms of ordinary dictionary significance are used.

Botanical classification: *Pelargonium×hortorum* cultivar Dueimvidared.

Parentage:

*Female parent.*—Proprietary selection of *Pelargonium×hortorum* identified as F-19-15, not patented.

*Male parent.*—Proprietary selection of *Pelargonium×hortorum* identified as F-04-09, not patented.

Propagation:

*Type cutting.*—Terminal vegetative cuttings.

*Time to initiate roots, summer.*—About 5 days at 20° C.

*Time to initiate roots, winter.*—About 7 days at 20° C.

*Time to develop roots, summer.*—About three weeks at 20° C.

*Time to develop roots, winter.*—About four weeks at 20° C.

*Root description.*—Fine, fibrous; white in color.

*Rooting habit.*—Freely branching.

Plant description:

*General appearance.*—Upright, somewhat outwardly spreading and rounded plant habit; densely foliated.

*Growth and branching habit.*—Vigorous growth habit. Freely branching, about three to five lateral branches per plant.

*Plant height.*—About 25 cm.

*Plant width.*—About 23 cm.

*Lateral branches.*—Length: About 8.5 cm. Internode length: About 1.4 cm. Texture: Smooth, glabrous. Color: 144A.

*Foliage description.*—Arrangement: Alternate, simple. Length: About 5.8 cm. Width: About 6.9 cm. Shape: Reniform. Apex: Rounded. Base: Cordate. Margin: Crenate. Venation pattern: Palmate. Texture, upper and lower surfaces: Smooth, glabrous. Color: Developing and fully expanded foliage, upper surface: 137A to 137B; venation, 144A. Developing and fully expanded foliage, lower surface: 138B; venation, 144A. Zonation pattern: Not visible. Petiole: Length: About 6.8 cm. Diameter: About 2 mm. Texture, upper and lower surfaces: Smooth. Color, upper and lower surfaces: 144A.

Flower description:

*Flower arrangement.*—Dark red-colored double flowers arranged in rounded hemispherical umbels arising from apical leaf axils. Umbels displayed above and beyond the foliage on peduncles. Flowers rounded in form. Umbels persistent, flowers not persistent. Flowers not fragrant.

*Quantity of flowers.*—Freely flowering; at full flower, plants have about six flower umbels with about 23 flowers per umbel.

*Flowering season.*—Flowering continuous spring through the summer. Plants begin flowering about eight weeks after planting.

*Flower longevity.*—Flowers last about five to seven days on the plant.

*Umbel size.*—Diameter: About 11.75 cm. Height: About 7 cm.

*Flower size.*—Diameter: About 4.9 cm. Depth (height): About 2 cm.

*Flower buds.*—Length: About 1.4 cm. Diameter: About 9 mm. Shape: Ovoid. Color: 144A.

*Petals.*—Quantity per flower: About five. Length: About 3 cm. Width: About 2.7 cm. Shape: Obovate. Apex: Rounded. Base: Attenuate. Margin: Entire; sinuate. Texture, upper and lower surfaces: Smooth. Color: When opening and fully opened, upper surface: 42A; color becoming closer to 45B with development. When opening and fully opened, lower surface: 43C.

*Petaloids.*—Quantity per flower: About two to four. Length: About 2.3 cm. Width: About 1.7 cm. Shape: Obovate. Apex: Rounded. Base: Attenuate. Margin: Entire; sinuate. Texture, upper and lower surfaces: Smooth. Color: When opening and fully opened, upper surface: 42A. When opening and fully opened, lower surface: 43C.

*Sepals.*—Quantity per flower: About five or six arranged in a single whorl. Length: About 1.1 cm. Width: About 3.4 mm. Shape: Elongated, tapering. Apex: Apiculate. Margin: Entire. Texture, upper and lower surfaces: Smooth; glabrous. Color, upper and lower surfaces: 144A.

*Peduncle* (*umbel stem*).—Length: About 11.2 cm. Diameter: About 1.5 cm. Angle: Mostly erect. Strength: Moderately strong. Texture: Smooth; glabrous. Color: 144A.

*Pedicel* (*individual flower stem*).—Length: About 3 cm. Diameter: About 1 mm. Angle: Mostly erect. Strength: Moderately strong. Texture: Pubescent. Color: 59A to 59B.

*Reproductive organs.*—Androecium: Anther quantity per flower: About ten. Anther length: About 2 mm. Anther shape: Ovate. Anther color: 47C. Pollen amount: Moderate. Pollen color: 28A. Gynoecium: Pistil quantity per flower: One. Pistil length: About 1 cm. Stigma shape: Five-parted, star-shaped. Stigma color: 60A to 60B. Style length: About 5 mm. Style color: 51B. Ovary color: Close to 144A.

*Seed/fruit.*—Development of seeds and fruit have not been observed.

Disease/pest resistance: Plants of the new Zonal *Geranium* have not been observed to be resistant to pathogens and pests common to Zonal *Geraniums*.

Temperature tolerance: Plants of the new Zonal *Geranium* have been observed to be tolerant to temperatures ranging from about 5° C. to about 40° C.

It is claimed:

1. A new and distinct cultivar of Zonal *Geranium* plant named 'Dueimvidared', as herein illustrated and described.

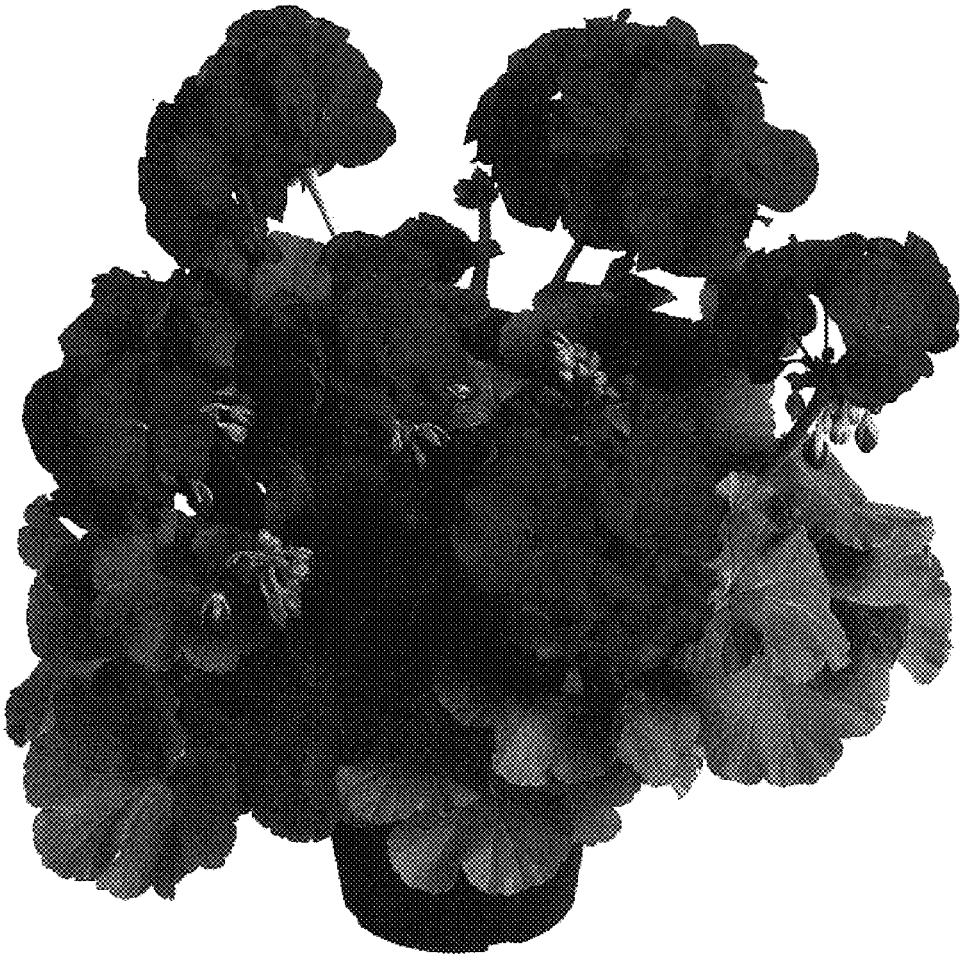

* * * * *